United States Patent [19]
Marks et al.

[11] Patent Number: 5,391,793
[45] Date of Patent: Feb. 21, 1995

[54] ARYLOXYALUMINOXANES

[75] Inventors: Tobin J. Marks; Xinmin Yang, both of Evanston, Ill.; Stanley B. Mirviss, Stamford, Conn.

[73] Assignees: Akzo Nobel N.V., Arnhem, Netherlands; Northwestern University, Evanston, Ill.

[21] Appl. No.: 969,920

[22] Filed: Nov. 2, 1992

[51] Int. Cl.$^6$ ............................................. C07F 5/06
[52] U.S. Cl. ...................................................... 556/179
[58] Field of Search ........................................... 556/179

[56] References Cited

U.S. PATENT DOCUMENTS

| | | | |
|---|---|---|---|
| 2,744,074 | 5/1956 | Theobald et al. | 260/2 |
| 3,242,099 | 3/1966 | Manyik et al. | 252/429 |
| 4,404,344 | 9/1983 | Sinn et al. | 526/160 |
| 4,544,762 | 10/1985 | Kaminsky et al. | 556/179 |
| 4,874,880 | 10/1989 | Miya et al. | 556/53 |
| 4,968,827 | 11/1990 | Davis | 556/179 |
| 5,003,095 | 3/1991 | Beard | 556/179 |
| 5,041,584 | 8/1991 | Crapo et al. | 556/179 |
| 5,235,081 | 8/1993 | Sangokoya | 556/179 |

FOREIGN PATENT DOCUMENTS

| | | | |
|---|---|---|---|
| 324856 | 6/1988 | European Pat. Off. | C08F 10/00 |
| 149949 | 9/1983 | Japan | C08L 85/00 |
| 271295 | 12/1991 | Japan | C07F 5/06 |
| 49293 | 2/1992 | Japan | C07F 5/06 |

OTHER PUBLICATIONS

Morrison et al., Organic Chemistry, 3rd Ed., Allyn and Bacon, Inc., Boston, Mass. (1973).
Chemical Abstracts, vol. 100, No. 8, Abs. No. 55893g (1984).
Chemical Abstracts, vol. 109, No. 25, Chem. Abs. No. 230,427t (1988).

*Primary Examiner*—José G. Dees
*Assistant Examiner*—Porfirio Nazario
*Attorney, Agent, or Firm*—Richard P. Fennelly; Louis A. Morris

[57] ABSTRACT

Aryloxyaluminoxanes containing the unit

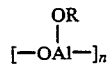

where R is unsubstituted or substituted aryl, such as phenyl or naphthyl, are useful as a cocatalysts in Ziegler-Natta and Kaminsky-type olefin polymerization catalysts. They can be formed by reaction of a source of water with an organoaluminum compound containing the desired aryloxy moiety or by reaction of preformed aluminoxane with an organic compound, such as a phenol, containing such a moiety.

3 Claims, No Drawings

ARYLOXYALUMINOXANES

BACKGROUND OF THE INVENTION

Aluminoxanes, for example, those of the general formula —(O—AlR)$_n$—, where R is an alkyl group, such as methyl, have received considerable attention in recent years due to their ability to form active olefin polymerization catalysts when combined with Group IV metallocenes. Among these, the most important aluminoxane is methylaluminoxane (R=methyl) since it produces the highest activity catalysts. Methylaluminoxane, however, is expensive since its synthesis requires the use of a rather expensive trimethylaluminum reagent. Furthermore, trimethylaluminum is very air- and moisture-sensitive and such factors make them less desirable for large scale industrial applications.

The disclosures in the art which cover aluminoxane compositions where R, as described above, can be selected from alkyl or, in some cases, aryl, all call for direct bonding of the R group to the aluminum atom. Examples of such disclosures include the following: U.S. Pat. Nos. 3,242,099 (R=C$_1$-C$_{12}$ alkyl or aryl); 4,404,344 (R=C$_1$-C$_5$ alkyl); 4,544,762 (R=C$_1$-C$_6$ alkyl); 4,665,208 (R=C$_1$-C$_8$ alkyl); 4,874,880 (R=hydrocarbyl such as C$_1$-C$_4$ alkyl); 5,041,584 (R=C$_2$ or higher alkyl); and European Patent Publication No. 324,856 (R=other than n-alkyl such as branched alkyl, cycloalkyl, or aryl).

Copending U.S. Ser. No. 853,466, filed Mar. 18, 1992, describes the manufacture of polymethylaluminoxane compositions of enhanced solution stability by reaction of the polymethylaluminoxane with certain organic compounds containing heteroatoms such as oxygen. Included as possible compounds are benzyl alcohol, nonyl phenol and butylated hydroxy toluene. The amount of such an organic compound is said to be no more than about 15 wt % of the polyaluminoxane, preferably up to about 10 wt %. Therefore, the resulting compositions, if an aryloxy-containing compound were selected, would contain a minor amount of aryloxy moieties.

SUMMARY OF THE INVENTION

The present invention relates to aryloxyaluminoxanes where an unsubstituted or substituted aryloxy group is directly bonded to the aluminum atom of an aluminoxane so that a predominant amount of aryloxy moieties, such as those comprising an —OC$_6$H$_5$ structure, are a substituent on aluminum.

DETAILED DESCRIPTION OF THE INVENTION

The term "aryloxyaluminoxane" as used herein is to be construed as covering aluminoxane compositions which are linear or cyclic and which contain the unit

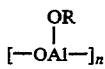

where n can be an integer of 2 or more and R is an unsubstituted or substituted aryl, such as a phenyl group or a naphthyl group. The phenyl group (R) is preferred and can contain at least one suitable electron withdrawing group such as halogen (fluoro, bromo, chloro, or iodo), nitro, trifluoromethyl, cyano, —C(O)R', where R' is alkyl, —C(O)OR", where R" is alkyl, aryl, and the like. A preferred selection for R is pentafluorophenyl. Alternatively, R can be substituted with such electron donating groups as alkyl, alkoxy, or aryloxy. The alkyl group(s) can be straight chain or branched and can contain from one to twelve carbon atoms.

The terminology "predominant", and grammatical variants, is intended to distinguish the present materials from those polymethylaluminoxanes described in U.S. Ser. No. 853,466 which contain relatively low amounts of aryloxy groups in certain embodiments (i.e., under about 15 wt %). In the compositions of the present invention a major amount of the aluminum atoms contain aryloxy substituents, preferably about 50% to substantially about 100%.

It is deemed that linear aluminoxanes in accordance with the present invention have the structure

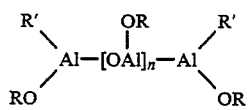

while cyclic aluminoxanes have the predominant structure

where R is unsubstituted or substituted aryl, such as phenyl, as described above, and R' can be lower alkyl, such as methyl, or hydroxyl. Both cyclic and acyclic (linear) structures can be present in the aluminoxane product.

The aryloxyaluminoxanes of this invention can be formed by reacting an organoaluminum compound containing the aryloxy group, for example, of the formula R$_2$AlOR', where R can be alkyl, for example, one containing from one to about eight carbon atoms, such as methyl and R' is unsubstituted or substituted aryl, with a source of water, such as liquid water or a compound, such as copper or sodium sulfate having water of crystallization, or silica or alumina, having water of absorption, which can supply the water.

An alternative way to make the aryloxyaluminoxanes of this invention is to react a conventional aluminoxane, such as methylaluminoxane with a reactive compound containing the desired unsubstituted or substituted aryloxy group, preferably a phenol.

The aryloxyaluminoxanes of this invention all have utility as cocatalysts for olefin polymerization in Ziegler-Natta and Kaminsky-type catalyst systems based on such catalyst components as unsupported titanium trichloride, supported titanium with and without donor, cyclopentadienyl titanium chlorides, and cyclopentadienyl and substituted cyclopentadienyl zirconium chlorides and alkyls. The Kaminsky-type systems are preferred. Suitable examples of these preferred systems include zirconocene dichloride, zirconocene dimethyl, bis(pentamethylcyclopentadienyl) dichloride or dimethyl, bis(indenyl) dimethyl, 2,2'-dimethyisila-bis(cyclopentadienyl) zirconium dimethyl, and the like. Still more examples of suitable catalyst components containing either zirconium or hafnium are presented in W. Kaminsky, *Shokubai*, 33, 536 (1991) and J. A. Swen et al., *Makromol. Chem., Makromol. Symp.*, 48/49, 253-295 (1991).

The present invention is further illustrated by the following Examples.

EXAMPLE 1

This Example illustrates synthesis of a phenoxyaluminoxane.

A solution of 1.2 g of $Me_2AlOC_6F_5$ (D. G. Hendershot et al., Organometallics, 1991, 10, 1917–1922) in toluene was slowly added to a toluene solution which contained $CuSO_4.5H_2O$ (0.4 g, 5 equivalents of OH) at $-40°$ C. The mixture was raised to room temperature over a period of two days with stirring. It was then filtered through a glass frit, and the toluene was removed under vacuum. A white solid was obtained in high yield. The $^1H$ NMR spectrum of this solid product in $C_6D_6$ showed no Al—$CH_3$ resonances. The $^{19}F$ NMR spectrum clearly revealed the presence of —$OC_6F_5$ groups.

EXAMPLE 2

This Example illustrates the use of the product from Example 1 as a cocatalyst in the polymerization of ethylene.

Fifteen milligrams of $Cp'_2ZrMe_2(Cp'=\eta^5-C_5Me_5)$ was mixed with 100 mg of the white solid obtained from Example 1 (Al/Zr=11) in 50 mL of dry toluene to yield a homogeneous solution. The solution was then exposed to ethylene (one atmosphere) for fifteen minutes with rapid stirring. After quenching the reaction with methanol, filtering, washing, and drying, 2.0 g of solid polyethylene was obtained.

EXAMPLE 3

This Example illustrates the use of the product from Example 1 as a cocatalyst in the polymerization of propylene.

Six milligrams of $Cp'_2ZrMe_2(CP'=\eta^5-C_5Me_5)$ and 12 mg of the white solid obtained from Example 1 (Al/Zr=3.5) were mixed in a quartz pressure tube. Then, 4 mL of dry toluene and 10 mL of liquid propylene were condensed into the above tube at $-78°$ C. The reaction mixture was stirred at $0°$ C. for one hour and then at room temperature for fifty minutes. The reaction was quenched with methanol, and the solvent was removed under vacuum. The polypropylene product (3.6 g) was collected by washing with acetone and drying under vacuum.

EXAMPLE 4

This Example illustrates the use of the product from Example 1 as a cocatalyst in the polymerization of propylene.

Six milligrams of $Cp'_2ZrMe_2(Cp'=\eta^5-C_5Me_5)$ and 36 mg of the white solid obtained from Example 1 (Al/Zr=10.5) were mixed in a quartz pressure tube. Then, 4 mL of dry toluene and 10 mL of liquid propylene were condensed into the above tube at $-78°$ C. The reaction mixture was stirred at $0°$ C. for twenty-five minutes. The reaction was quenched with methanol. After removing the solvent, the polypropylene product (3.4 g) was collected by washing with acetone and drying under vacuum.

EXAMPLE 5

This Example illustrates a second route for the synthesis of phenoxyaluminoxanes.

A commercial sample of methylaluminoxane (MAO, 0.60 g) was dissolved in 50 mL of toluene in a 500 mL flask and was cooled to $-55°$ C. A solution of pentafluorophenol (1.85 g) in 20 mL of toluene was then added dropwise to the above solution. It was slowly warmed to room temperature and stirred for ten hours. A white solid in quantitative yield was collected after removing solvent under vacuum.

EXAMPLE 6

This Example illustrates the use of the product from Example 5 as a cocatalyst in the polymerization of propylene.

Six milligrams of $Cp'_2ZrMe_2(Cp'=\eta^5-C_5Me_5)$ and 40 mg of the white solid obtained from Example 5 (Al/Zr=12) were mixed in a 50 mL flask. Then 20 mL of propylene was condensed in at $-78°$ C. The reaction mixture was stirred at $0°$ C. for three hours. The reaction was quenched with methanol. Solvent was then removed under vacuum. After washing and drying, 3.3 g of polypropylene was collected.

EXAMPLE 7

This Example illustrates the use of the product from Example 5 as a cocatalyst in the isotactic polymerization of propylene.

Six milligrams of $Me_2Si(C_5Me_4)(C_5H_3R^*)ZrMe_2(R^*=(+)$-neomenthyl) and 31 mg of the white solid obtained from Example 5 (Al/Zr=12.5) were mixed in a 50 mL flask. Then 20 mL of dry propylene was condensed in at $-78°$ C. The reaction mixture was stirred at $0°$ C. for three hours. A reaction was quenched with methanol. Solvent was then removed under vacuum. After washing and drying, 0.80 g of white solid polypropylene was collected, and $^{13}C$ NMR (1,2,4-trichlorobenzene, $130°$ C.) showed the "mmmmm" pentad in this material at greater than 90%.

EXAMPLES 8–13

The Table set forth below gives the results of propylene polymerizations conducted at $30°$ C., one atmosphere, in 250 ml of toluene using two differing zirconium-containing metallocenes with various aluminoxanes at a 250:1 molar ratio of Al:Zr. All values are given in terms of $10^5$ polypropylene/mole Zr.hr.atm:

| Metallocene | PMAO[1] | $Me_2AlO\phi F_5$ $H_2O$[2] | $Me_2AlO\phi F_5$ + $CuSO_4 \cdot 5H_2O$[3] |
|---|---|---|---|
| $Cp_2ZrMe_2$ | 0.40[4] | 0.40 | 1.13[5] |
| $Cp_2ZrCl_2$ | 1.35[6] | 0.81 | 1.07 |

[1] PMAO = polymethylaluminoxane. Used as a control and not as part oF the present invention.
[2] The molar ratio of water to aluminum was 0.4:1.
[3] The molar ratio oi water to aluminum was 1:1.
[4] Average of six runs.
[5] Average of runs of 1.07 and 1.19.
[6] Average of five runs.

EXAMPLES 14–17

The following propylene polymerization data was generated analogous to that shown in Examples 8–13 using less aluminoxane and a higher zirconium content (a 25:1 ratio of Al:Zr):

| Metallocene | $Me_2AlO\phi F$ + $H_2O$[1] | $Me_2AlO\phi F_5$ + $CuSO_4 \cdot 5H_2O$[2] |
|---|---|---|
| $Cp_2ZrMe_{22}$ | 0.13 | 0.28 |
| $Cp_2ZrCl_2$ | 0.15 | 0.22 |

[1] The molar ratio of water to aluminum was 0.4:1.
[2] The molar ratio of water to aluminum was 1:1.

EXAMPLES 18-20

The Table set forth below gives the results ($10^5$ g polypropylene/mole Zr.hr.atm) of other polymerizations of propylene at 30° C., one atmosphere, 250 ml toluene, and 250:1 ratio of Al:Zr:

| Aluminoxane Used | Metallocene Used | |
|---|---|---|
| | $Cp_2ZrMe_2$ | $Cp_2ZrCl_2$ |
| $Et_2AlO\phi F_5 + H_2O$ (0.5:1)[2] | 0.80[1] | 0.81 |
| $(iBu)_2AlO\phi F_5 + H_2O$ (0.4:1)[2] | 0.60 | — |

[1] Average of runs of 0.71 and 0.89.
[2] This indicates the molar ratio of water to aluminum.

EXAMPLES 21-23

Ethylene polymerizations were conducted at 80° C., three atmospheres pressure, in 250 ml of toluene, with a $3.14 \times 10^5$ molar ratio of Al:Zr using dicyclopentadienyl zirconium dichloride as the metallocene:

| Aluminoxane Used | Productivity[1] |
|---|---|
| PMAO | 2.35[2] |
| $Me_2AlO\phi F_5 + H_2O$ (0.4:1) | 1.11 |
| $(iBu)_2AlO\phi F_5 + H_2O$ | 0.70 |

| Aluminoxane Used | Productivity[1] |
|---|---|
| | (0.4:1) |

[1] Measured as $10^6$ gm. PE/ gm. Zr hr. atm.
[2] Average of eight runs.

EXAMPLE 24

This Example is similar to Examples 21-22 but utilizes a phenoxy group with electron donating substituents on the phenyl ring. The product of the reaction of triisobutylaluminum and 2,6-di-t-butyl-paracresol (1:1 mole ratio), or 2,6-di-t-butyl-4-methyl-phenoxide, was converted to an aluminoxane with water (0.65:1 water to aluminum mole ratio). This aluminoxane was used in ethylene polymerization with zirconocene dichloride under the same reaction conditions used in Examples 21-22. The polyethylene produced amounted to $0.51 \times 10^6$ g. PE/g. Zr.hr.atm.

The foregoing Examples, since they are intended to merely set forth only certain embodiments of the present invention, should not be construed in a limiting sense. The scope of protection sought is set forth in the claims which follow.

We claim:

1. A process for forming a composition of matter which predominantly comprises aryloxyaluminoxane which comprises reacting an organoaluminum compound containing the aryloxy group with a source of water.

2. A process as claimed in claim 1 wherein the source of water is water of crystallization or water of absorption.

3. A process as claimed in claim 1 wherein the source of water is liquid water.

* * * * *